US008864750B2

(12) United States Patent
Ross et al.

(10) Patent No.: US 8,864,750 B2
(45) Date of Patent: Oct. 21, 2014

(54) TOOL AND METHOD FOR EXTERNAL FIXATION STRUT ADJUSTMENT

(75) Inventors: John D. Ross, Dallas, TX (US); Mikhail L. Samchukov, Dallas, TX (US); Alexander M. Cherkashin, Dallas, TX (US); John G. Birch, Dallas, TX (US)

(73) Assignee: Texas Scottish Rite Hospital for Children, Dallas, TX (US)

( * ) Notice: Subject to any disclaimer, the term of this patent is extended or adjusted under 35 U.S.C. 154(b) by 896 days.

(21) Appl. No.: 12/865,248

(22) PCT Filed: Feb. 18, 2009

(86) PCT No.: PCT/US2009/034413
§ 371 (c)(1),
(2), (4) Date: Jul. 29, 2010

(87) PCT Pub. No.: WO2009/105479
PCT Pub. Date: Aug. 27, 2009

(65) Prior Publication Data
US 2011/0004199 A1    Jan. 6, 2011

Related U.S. Application Data

(60) Provisional application No. 61/029,483, filed on Feb. 18, 2008.

(51) Int. Cl.
*A61B 17/00*    (2006.01)
(52) U.S. Cl.
USPC .................................. 606/1; 606/56; 606/130
(58) Field of Classification Search
USPC ................................................ 606/1, 54–59
See application file for complete search history.

(56) References Cited

U.S. PATENT DOCUMENTS

| 2,238,870 A | 4/1941 | Haynes |
| 2,346,346 A | 4/1944 | Anderson |
| 4,308,863 A | 1/1982 | Fischer |

(Continued)

FOREIGN PATENT DOCUMENTS

| CA | 2633944 A1 | 7/2007 |
| DE | 3802743 A1 | 8/1989 |

(Continued)

OTHER PUBLICATIONS

International Search Report, PCT/US2009/034413, dated Apr. 15, 2009, 1 page.

(Continued)

*Primary Examiner* — Gary Jackson
*Assistant Examiner* — Jeffrey Lipitz
(74) *Attorney, Agent, or Firm* — Baker & McKenzie LLP

(57) ABSTRACT

The present disclosure includes a method for adjusting the orientation of a first external fixator support member relative to a second external fixator support member, wherein a plurality of adjustable struts connect the first and second external fixator support members. The method include providing a programmable tool, and storing, in a memory unit of the tool, instructions for adjusting the length of each of the plurality of adjustable struts to a desired length. The method further includes receiving identification information corresponding to a first adjustable strut and retrieving, from the memory unit, the instructions for adjusting the length of the first adjustable strut. The method also includes activating an actuator of the tool to adjust the length of the first adjustable strut according to the retrieved instructions. Various embodiments of the programmable tools are also included in the present disclosure.

19 Claims, 6 Drawing Sheets

(56) References Cited

U.S. PATENT DOCUMENTS

| | | |
|---|---|---|
| 4,365,624 A | 12/1982 | Jaquet |
| 4,621,627 A | 11/1986 | DeBastiani et al. |
| 4,768,524 A | 9/1988 | Hardy |
| 4,889,111 A | 12/1989 | Ben-Dov |
| 4,973,331 A | 11/1990 | Pursley et al. |
| 4,988,244 A | 1/1991 | Sheldon et al. |
| 5,019,077 A | 5/1991 | De Bastiani et al. |
| 5,095,919 A | 3/1992 | Monticelli et al. |
| 5,156,605 A | 10/1992 | Pursley et al. |
| 5,180,380 A | 1/1993 | Pursley et al. |
| 5,458,599 A | 10/1995 | Adobbati |
| 5,533,418 A | 7/1996 | Wu et al. |
| 5,702,389 A | 12/1997 | Taylor et al. |
| 5,728,095 A | 3/1998 | Taylor et al. |
| 5,776,132 A | 7/1998 | Blyakher |
| 5,863,292 A | 1/1999 | Tosic |
| 5,885,283 A | 3/1999 | Gittleman |
| 5,891,143 A | 4/1999 | Taylor et al. |
| 5,928,230 A | 7/1999 | Tosic |
| 5,971,984 A | 10/1999 | Taylor et al. |
| 6,030,386 A | 2/2000 | Taylor et al. |
| 7,282,052 B2 | 10/2007 | Mullaney |
| RE40,914 E | 9/2009 | Taylor et al. |
| 8,029,505 B2 | 10/2011 | Hearn et al. |
| 8,202,273 B2 | 6/2012 | Karidis |
| 8,257,353 B2 | 9/2012 | Wong |
| 8,296,094 B2 | 10/2012 | Harrison et al. |
| 8,333,766 B2 | 12/2012 | Edelhauser et al. |
| 8,366,710 B2 | 2/2013 | Hirata et al. |
| 8,377,060 B2 | 2/2013 | Vasta et al. |
| 8,388,619 B2 | 3/2013 | Mullaney |
| 2002/0010465 A1 | 1/2002 | Koo et al. |
| 2003/0149378 A1 | 8/2003 | Peabody et al. |
| 2003/0191466 A1 | 10/2003 | Austin et al. |
| 2003/0199856 A1 | 10/2003 | Hill et al. |
| 2003/0212398 A1 | 11/2003 | Jackson |
| 2004/0073211 A1 | 4/2004 | Austin et al. |
| 2004/0097922 A1 | 5/2004 | Mullaney |
| 2004/0116926 A1 | 6/2004 | Venturini et al. |
| 2005/0192572 A1 | 9/2005 | Abdelgany et al. |
| 2005/0215997 A1 | 9/2005 | Austin et al. |
| 2005/0234457 A1 | 10/2005 | James et al. |
| 2006/0052782 A1 | 3/2006 | Morgan et al. |
| 2006/0207118 A1 | 9/2006 | Kim |
| 2006/0235389 A1 | 10/2006 | Albert et al. |
| 2007/0055234 A1 | 3/2007 | McGrath et al. |
| 2007/0055254 A1 | 3/2007 | Ihde |
| 2007/0083087 A1 | 4/2007 | Carda |
| 2007/0085496 A1 | 4/2007 | Philipp et al. |
| 2007/0225704 A1 | 9/2007 | Ziran et al. |
| 2007/0233134 A1 | 10/2007 | Bastian et al. |
| 2008/0021451 A1 | 1/2008 | Coull et al. |
| 2009/0036890 A1 | 2/2009 | Karidis |
| 2009/0036892 A1 | 2/2009 | Karidis et al. |
| 2010/0087819 A1 | 4/2010 | Mullaney |
| 2010/0262160 A1 | 10/2010 | Boyden et al. |
| 2010/0262239 A1 | 10/2010 | Boyden et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0004199 A1 | 1/2011 | Ross et al. |
| 2011/0118738 A1 | 5/2011 | Vasta et al. |
| 2011/0166572 A1 | 7/2011 | Ihde |
| 2011/0313418 A1 | 12/2011 | Nikonovas |
| 2011/0313419 A1 | 12/2011 | Mullaney |
| 2012/0041439 A1 | 2/2012 | Singh et al. |
| 2012/0130384 A1 | 5/2012 | Henderson |
| 2012/0303028 A1 | 11/2012 | Wong |
| 2012/0303029 A1 | 11/2012 | Vasta et al. |
| 2013/0018374 A1 | 1/2013 | Edelhauser et al. |

FOREIGN PATENT DOCUMENTS

| | | |
|---|---|---|
| DE | 9316164 U1 | 7/1994 |
| DE | 4421223 A1 | 12/1995 |
| DE | 102007026404 A1 | 12/2008 |
| EP | 0029298 A1 | 5/1981 |
| EP | 1239784 B1 | 4/2006 |
| EP | 1916952 B1 | 12/2009 |
| EP | 2134515 B1 | 7/2010 |
| EP | 2417923 A1 | 2/2012 |
| GB | 421788 | 12/1934 |
| GB | 2229096 A | 9/1990 |
| IT | 1259768 B | 3/1996 |
| JP | S52-003290 | 8/1978 |
| JP | S63-500499 | 2/1988 |
| JP | H02180254 A | 7/1990 |
| JP | H10290807 A | 11/1998 |
| JP | 2003508108 A | 3/2003 |
| JP | 2003508150 A | 3/2003 |
| JP | 2005-137586 | 6/2005 |
| WO | 9222268 A1 | 12/1992 |
| WO | 9626678 A1 | 9/1996 |
| WO | 9730650 A1 | 8/1997 |
| WO | 9812975 A2 | 4/1998 |
| WO | 9815231 A1 | 4/1998 |
| WO | 9920193 A1 | 4/1999 |
| WO | 9947060 A1 | 9/1999 |
| WO | 9948414 A2 | 9/1999 |
| WO | 0003647 A1 | 1/2000 |
| WO | 0115611 A1 | 3/2001 |
| WO | 0122892 A1 | 4/2001 |
| WO | 03086211 A1 | 10/2003 |
| WO | 03086212 A2 | 10/2003 |
| WO | 03086213 A2 | 10/2003 |
| WO | 2004026103 A2 | 4/2004 |
| WO | 2007002180 A2 | 1/2007 |
| WO | 2007060507 A2 | 5/2007 |
| WO | 2007139031 A1 | 12/2007 |
| WO | 2008002992 A1 | 1/2008 |
| WO | 2008134624 A1 | 11/2008 |
| WO | 2009018349 A2 | 2/2009 |
| WO | 2009018398 A2 | 2/2009 |
| WO | 2009100247 A1 | 8/2009 |
| WO | 2009100459 A1 | 8/2009 |
| WO | 2009102904 A1 | 8/2009 |
| WO | 2009105479 A1 | 8/2009 |
| WO | 2010042619 A1 | 4/2010 |
| WO | 2010104567 A1 | 9/2010 |
| WO | 2010120367 A1 | 10/2010 |
| WO | 2011017321 A2 | 2/2011 |
| WO | 2011060264 A1 | 5/2011 |
| WO | 2011060266 A1 | 5/2011 |
| WO | 2011106507 A1 | 9/2011 |
| WO | 2011146703 A1 | 11/2011 |
| WO | 2011163406 A2 | 12/2011 |

OTHER PUBLICATIONS

International Preliminary Report on Patentability, PCT/US2009/034413, dated Aug. 24, 2010, 7 pages.

Extended European Search Report, Application No. 09712412.7-1526, PCT/US2009/034413, dated Dec. 3, 2012, 10 pages.

International Search Report, PCT/US2010/056541, dated Jan. 12, 2011, 1 page.

International Preliminary Report on Patentability, PCT/US2010/056541, Date of issuance May 15, 2012, 7 pages.

International Preliminary Report on Patentability, PCT/US2010/056539, Date of issuance May 15, 2012, 9 pages.

International Search Report, PCT/US2010/056539, Dated Jan. 18, 2011, 2 pages.

Steffen Schumann ,et al., "Calibration of X-ray radiographs and its feasible application for 2D/3D reconstruction of the proximal femur" (2008), 4 pages.

Jetzki S., et al., "Fluoroscopy-Based 3-D Reconstruction of Femoral Bone Cement: A New Approach for Revision Total Hip Replacement," (2005), 12 pages.

Guoyan Zheng, et al., "3-D reconstruction of a surface model of the proximal femur from digital biplanar radiographs," (2008), 4 pages.

(56) References Cited

OTHER PUBLICATIONS

Laporte S., et al., "A biplanar reconstruction method based on 2D and 3D contours: application to the distal femur," (2003), 6 pages.
Japanese Office Action, JP Application No. 2010-546960, dated Mar. 12, 2013, 4 pages.
Japanese Office Action, JP Application No. 2010-546904, dated Mar. 12, 2013, 6 pages.
Japanese Office Action, JP Application No. 2010-546098, dated Mar. 5, 2013, 11 pages.
International Preliminary Report on Patentability, PCT/RU2010/000452, dated Feb. 26, 2013, 9 pages.
Japanese Office Action, JP Application No. 2010-545284, dated Mar. 5, 2013, 6 pages.
European Extended Search Report, Application No. 09707791.1-1654 / 2240084, PCT/US2009/033258, dated Nov. 21, 2013, 6 pages.
Japanese Office Action, dated Nov. 26, 2013, JP Application No. 2010-545284, 4 pages.
Extended European Search Report, EP 09708841.3-1654 / 2240085; PCT/US2009/033603, dated Dec. 2, 2013, 5 pages.
Japanese office action, JP Application No. 2010-546904, dated Oct. 29, 2013, 4 pages.
International Search Report and Written Opinion, PCT/US2013/064067, dated Jan. 31, 2014, 7 pages.
International Search Report and Written Opinion, PCT/RU2013/000203, dated Jan. 29, 2014, 23 pages.
Canero, C., et al., "Predictive (Un)distortion Model and 3-D Reconstruction by Biplane Snakes, IEEE Transactions on Medical Imaging," vol. 21, No. 9, (Sep. 2002), 14 pages.
Ghanem, R.N., et al., "Heart-Surface Reconstruction and ECG Electrodes Localization Using Fluoroscopy, Epipolar Geometry and Stereovision: Application to Noninvasive Imaging of Cardiac Electrical Activity," IEEE Transactions on Medical Imaging, vol. 22, No. 10, (Oct. 2003), 12 pages.
Li, Y., et al., "Distortion Correction and Geometric Calibration for X-Ray Angiography System," IEEE Transactions on Nuclear Science, vol. 56, No. 3, (Jun. 2009), 12 pages.
Selby, B.P., et al., "Patient positioning with X-ray detector self-calibration for image guided therapy," Australas Phys. Eng. Sci. Med., vol. 34, (2011), 10 pages.
Yang, J., et al., "Novel Approach for 3-D Reconstruction of Coronary Arteries From Two Uncalibrated Angiographic Images," IEEE Transactions on Image Processing, vol. 18, No. 7, (Jul. 2009), 10 pages.
Zheng, G., et al., "A 2D/3D correspondence building method for reconstruction of a patient-specific 3D bone surface model using point distribution models and calibrated X-ray images," Medical Image Analysis, vol. 13, (2009), 17 pages.
European Extended Search Report, EP Application No. 09710983.9-1654/2249721 PCT/US2009/033975, dated Apr. 4, 2014, 7 pages.

TOOL AND METHOD FOR EXTERNAL FIXATION STRUT ADJUSTMENT

TECHNICAL FIELD

The present application relates in general to the field of external fixation, and more specifically, to tools used for the adjustment of external fixator connection strut or other connection rods.

BACKGROUND

Without limiting the scope of the disclosure, its background is described in connection with external fixation devices and specifically tools used for the adjustment of external fixator struts or other connection rods.

Generally, external fixation devices are commonly used in a variety of surgical procedures including limb lengthening and deformity correction. The process involves a rigid framework comprising several rings that are placed externally around the limb and attached to bone segments using wires and half pins inserted into the bone segments and connected to the related sections of the external rigid framework. The opposite rings of the rigid framework are interconnected by either threaded or telescopic rods directly or in conjunction with uni-planar or multi-planar hinges, which allow the surgeon to adjust position of the rings relative to each other longitudinally, rotationally, horizontally or angularly over a period of time.

For example, in limb lengthening, the bone is surgically divided into two segments and wires and half pins are inserted into bone segments above and below the surgical bone cut and attached to rings of a rigid framework interconnected by struts or threaded and telescopic connection rods. The rigid framework is used to gradually push the two bone segments apart longitudinally over a period of time (e.g., one millimeter a day). This allows the bone to gradually form in the gap between bone segments created by this distraction technique. Once the desired amount of lengthening is achieved (e.g., 5-6 cm), the external apparatus is stabilized into a fixed position and left on the bone segments until complete mineralization of the newly formed bone (e.g., 3-6 months, depending on the nature of pathology and amount of lengthening).

Similarly, in deformity correction, the bone is surgically divided into two segments (usually at the apex of the deformity) and wires and half pins are inserted into bone segments above and below the surgical bone cut and attached to rings of a rigid framework. Opposite rings of the rigid framework are connected together by threaded rods with attached uni-planar or multi-planar hinges that are used to gradually push the two bone segments apart angularly over a period of time.

One common fixation device is a circular metal structure known as the Ilizarov Apparatus. The Ilizarov apparatus, when used for limb lengthening or deformity correction, consists of several rings or arches that are placed externally around the limb and attached to surgically separated bone segments using wires and half pins. For limb lengthening, the opposite rings are interconnected directly by three or four threaded or telescopic rods that are regularly adjusted in length and allowed for gradual separation of bone segments longitudinally. For angular deformity correction, the opposite rings of the Ilizarov apparatus are connected by a pair of hinges that provide an axis of rotation for bone segments and one angular distractor that gradually pushes two rings and associated bone segments apart.

Another common external fixation device is the Taylor Spatial Frame, which is a hexapod type of the external fixation device based on a Stewart platform but shares many components and features of the Ilizarov apparatus. The Taylor Spatial Frame consists of two external fixation rings attached to bone segments by wires and half pins and connected together by 6 telescopic struts with multi-planar hinges located at both ends of the strut. Each strut may be lengthened or shortened as necessary to either pull two interconnected ring segments towards each other or push them apart. Adjustment of strut length allows manipulating with bone segments acutely or gradually in 6 axes (e.g., lengthening/shortening external/internal rotation, anterior/posterior horizontal translation, medial/lateral horizontal translation, anterior/posterior angular translation, and medial/lateral angular translation) to perform limb lengthening and correct angular, translational and rotational deformities simultaneously.

An amount of an external fixator strut or connection rod length adjustment depends on the amount of bone segment separation to produce a reliable distraction regenerate. Generally, for limb lengthening and deformity correction the optimal daily amount of bone segment separation was determined as 1 mm divided into at least 4 increments per day. Therefore in cases with limb lengthening using 3-4 parallel threaded or telescopic rods or deformity correction using one threaded or telescopic rod (e.g., Ilizarov apparatus), the length of each rod is adjusted ¼ of a millimeter four times a day producing a total length increase of 1 mm per day. It has also been suggested that smaller movements using a high frequency rate of distraction (e.g., a rate of distraction of from 1/60 to 1/1440 of a millimeter 60 to 1440 times a day) prevents soft tissue damage and produces even better results.

In cases with limb lengthening and deformity correction using six struts (e.g., Taylor Spatial Frame), the amount of daily strut length adjustment is calculated by special software. Once the apparatus is attached to the bone segments, numerous parameters such as rings diameter, initial strut length, strut location and so forth are entered into the software to characterize one ring position relative to another ring and position of bone segments relative to each other and to the rings. After calculation of the total amount of each strut length adjustment, the software provides a tabled instruction ("prescription") on the amount of each strut length adjustment that should be achieved per each increment including strut number, the exact amount of adjustment necessary and the time to make the adjustment. In most of the cases with deformity correction, the struts are adjusted in different directions (shortening/lengthening) and in the different amounts.

External fixator strut (or other connection threaded or telescopic rod) length adjustments are usually made by the patient (parents) either by turning the adjustment knob of the struts or telescopic rods manually or by turning the nuts of the threaded rods with a regular (e.g., open end) wrench. This way of strut length adjustment is time consuming (e.g., due to loosening and retightening of the threaded rod nuts before and after each adjustment), does not provide precise length adjustment (e.g., due to difficulty to monitor small amounts of adjustments) and creates overall frame instability during adjustments (e.g., due to dimensional clearance between connection elements). Furthermore, the prescription for length adjustments can be complicated, and human errors are prone to occur during the course of a complicated prescription. Additionally, existing adjustment processes do not include any feedback to the doctors or patient to confirm the desired adjustments have been properly and accurately made.

SUMMARY

As a consequence of the foregoing, a longstanding need exists among users for a method and apparatus that more precisely controls the incremental adjustment in length of the external fixator struts or other connection rods.

The present application describes a method and a programmable tool for incrementally adjusting the length of the external fixator strut or other connection rod of an external fixation device. The tool has a housing, a strut identifier, a microcontroller with an internal memory, a control board, a power source, a motor, a gear box and a rotating shaft and is adapted to engage the adjustment mechanism of the external fixator strut and rotate the adjustment mechanism the preprogrammed direction and amount of turns to adjust the position of the threaded elongated member relative to the adjustment mechanism of the external fixator strut and thereby automatically adjust the overall end-to-end length of the external fixator strut the prescribed amount.

The present application describes a programmable tool for adjusting an external fixation strut. The programmable tool includes a power supply disposed in the housing, a data port disposed at least partially within the housing, and a signal-sensor disposed at least partially within the housing for receiving a signal from an external source. A motor is disposed within the housing and a gear box positioned between an output shaft and the motor with a strut fitting is adapted to fit an external fixation strut in operable communication with the output shaft motor for adjusting the external fixation strut. A controller is in electrical communication with the data port, the signal-sensor, the power supply and the motor. Also described is a memory unit in electrical communication with the controller to store one or more strut adjustment parameters, a display in electrical communication with the controller and a control panel in electrical communication with the controller to control one or more operations of the programmable tool.

The present application also describes a programmable tool for adjusting an external fixation strut having a data port disposed at least partially within the housing, a signal-sensor disposed at least partially within the housing for receiving a signal from an external source, a power supply, a motor disposed within the housing, an output shaft comprising a strut fitting in operable communication with the motor, wherein the strut fitting is adapted to fit an external fixation strut and a controller in electrical communication with the data port, the signal-sensor, the power supply and the motor.

Described in the present disclosure also includes a method for adjusting the orientation of a first external support member relative to a second external support member, in which a plurality of adjustable struts connect the first and second external support members. The plurality of struts include a first adjustable strut having an initial length, and the method includes providing a programmable tool, the programmable tool comprising a controller in electrical communication with a memory unit and an actuator. The actuator is operable to engage the plurality of adjustable struts and adjust the length of the plurality of adjustable struts. The method further includes storing, in the memory unit, instructions for adjusting the length of each of the plurality of adjustable struts to a desired length. The method further includes receiving identification information corresponding to the first adjustable strut, and retrieving, from the memory unit, the instructions for adjusting the length of the first adjustable strut based on the identification information corresponding to the first adjustable strut. Finally, the disclosed method includes activating the actuator to adjust the length of the first adjustable strut according to the retrieved instructions.

In some embodiment, the programmable tool further include a measuring device for measuring the length of the plurality of adjustable struts, and the method further comprises determining the length of the first adjustable strut prior to and after adjusting the length of the first adjustable strut; and confirming that the first strut has the desired length. In an exemplary, the measuring device is a digital rule.

BRIEF DESCRIPTION OF THE DRAWINGS

For a more complete understanding of the features and advantages of the present disclosure, reference is now made to the detailed description of the disclosure along with the accompanying figures and in which.

DETAILED DESCRIPTION

While the making and using of various embodiments of the present disclosure are discussed in detail below, it should be appreciated that the present application provides many applicable inventive concepts that can be embodied in a wide variety of specific contexts. The specific embodiments discussed herein are merely illustrative of specific ways to make and use the disclosure and do not delimit the scope of the disclosure.

Figure 1:
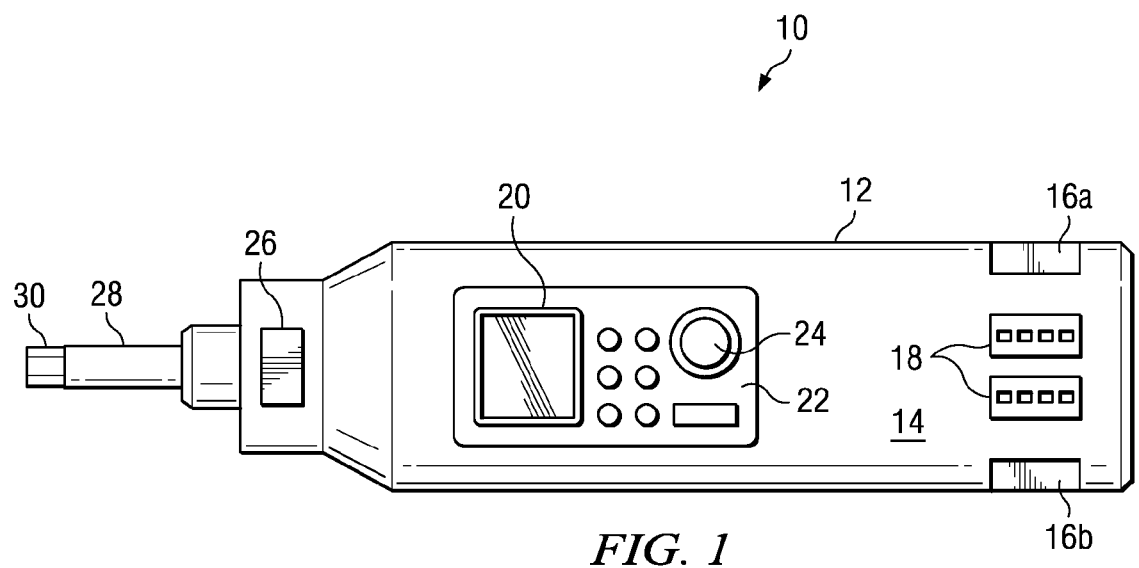
FIG. 1 is a perspective view of one embodiment of a programmable tool for external fixator strut length adjustment.

FIG. 1 is a perspective view of one embodiment of a programmable tool for external fixator strut length adjustment. The programmable tool 10 includes a housing having a front 14 and a back (not shown). The shape of the housing 12 may be in any shape and size convenient for use. For example, the housing 12 may be cylindrical in shape, square in shape, ergonomic in shape etc. and may be of a size convenient for use by children or adults. In addition, the housing may be ergonomically shaped or shaped and sized for use by the elderly, handicapped or disabled.

The housing may have a variety of connections ports, connectors, displays and controls. For example in one embodiment the housing 12 has a power connection 16a and 16b to provide a source of external power to recharge the batteries (not shown) used to provide power to the programmable tool 10. The power connection 16a and 16b may be positioned to fit into a docking station (not shown) when not in use. Although the power connection 16a and 16b are shown located on the sides of the housing 12, the skilled artisan will recognize that the power connection 16a and 16b may be located on the same side bottom or numerous combinations thereof without affecting the function of the programmable tool 10. Alternatively, the power connection 16a and 16b may be in the form of a female connection (not shown) or a male connection (not shown) to allow the power source to be plugged into the housing. Still other embodiments may include battery packs that may be positioned in the housing 12 so that they may be easily removed, recharged and replaced. Alternatively, the batteries may be disposable and replaced as necessary. The programmable tool 10 may also have an internal battery and/or memory storage device to retain information in memory in case of a loss in power. Generally, the power source can be a battery, a solar panel, a layer of piezoelectric film or any type of energy harvesting technology. The power source can also be a combination of a battery along with one of the voltage generators connected to a power controller to manage power consumption and storage in the battery.

The housing 12 also has one or more data ports 18 that allow communication between the programmable tool 10 and an external source, e.g., computer, etc. The one or more communication or data ports 18 are connected to the internal circuitry (not shown) of the programmable tool 10. Generally, the one or more data ports 18 are in communication with the controller. The present application comprises a microcontroller, processor, microprocessor or analog circuit or logic circuit, an external sensor, a sensor reader, a transmitter, a receiver, output interface, a battery, a motor, a gearbox, a data storage, a memory, a communication device/port, a data port, or other components. In addition, the microprocessor determines whether one or more operational parameters are within one or more guidelines, the specific strut, the specific length of the strut, the specific location of the strut and determines the output necessary given the specific treatment regiment. The processor or analog circuit can receive instructions and/or relay information to and from medical service providers via the communications port. The processor or analog circuit can direct output to the motor and/or the display as necessary.

The one or more data ports 18 may be in the form of a USB port, mini port, micro port RS232 port, telephone connection port, Ethernet port, CAT 5 connection port, or other port known to the skilled artisan to allow transfer of information and data in a uni-, bi- or multi-directional manner. Although, the one or more data ports 18 are shown in the form of a physical connection, the skilled artisan will immediately recognize that other forms of communication are acceptable. For example, the one or more data ports 18 may be in the form of an internal modem, cellular modem, Wi-Fi module, Bluetooth module, IR module, RF module, RFID module and other methods known to the skilled artisan to allow transfer of information and data in a uni-, bi- or multi-directional manner.

The housing 12 includes a display 20 which may display various types of information. For example, the display 20 may be in the form of a visual display (e.g., LCD, LEDs, Arrays of LEDs, or other visual display known to those skilled in the art), a speaker, a multi-tone generator, a communications interface or a combination thereof. The visual display can be a set of light emitting diodes that provide a feedback to the user, a status of the strut, other relevant information or a combination thereof.

The housing 12 also includes a control board 22 that has various controls to allow the user to operate various functions of the device. For example, the control board 22 may include selectors for the specific struts, buttons to set the time, date, etc. and other selectors that allow programming or operation of various functions in conjunction with the display 20. The control board 22 may also include an on/off switch 24 that may be used to operate the programmable tool 10.

A strut sensor 26 is incorporated into the housing 12 to allow the automatic recognition of the specific strut to be adjusted. In some embodiments, each strut includes a device for providing a signal that embodies an unique identification code. The strut sensor either wirelessly or electrically communicates with the signal emitting device to receive the unique identification code. The unique identification code allows the programmable tool 10 to recognize and identify the strut, and may be in various forms described in the present disclosure or known in the art. For example, the strut sensor 26 may be an RFID sensor that receives a unique radiofrequency identification code from the strut to identify the strut on the external fixation device. In some embodiments where multiple external fixation devices are used (either on a single individual or multiple individuals), the strut sensor 26 may identify the individual and each specific strut on the external fixation device. As such, the use of an unique identification code allows the use of a single programmable tool 10 with numerous individuals and/or numerous external fixation devices.

The housing 12 has a rotating shaft 28 that extends from the housing 12 and terminates in a strut fitting 30 that allows the connection of the programmable tool 10 to the external fixation strut. The rotating shaft 28 may be enclosed in a separate covering leaving only the strut fitting 30 exposed and accessible, while protecting the actual rotating shaft 28.

Figure 2:
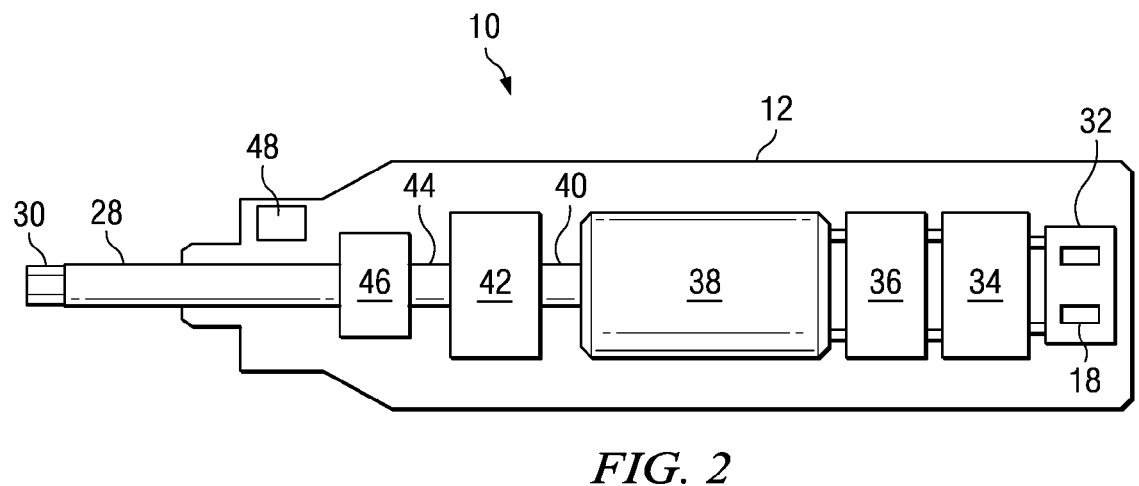
FIG. 2 is a cross sectional view of one embodiment of a programmable tool for external fixator strut length adjustment.

FIG. 2 is a cross sectional view of one embodiment of a programmable tool for external fixator strut length adjustment. The housing 12 may be sized to fit a variety of individual modules. For example, the housing may include a data port 18 accessible from the exterior of the programmable tool 10 and in communication with a data module 32. In some embodiments, the data module 32 stores instructions for adjusting the struts. For example, a prescription table may be received and stored in the data module 32 for later retrieval. The data module 32 is in communication with a microcontroller 34 that includes numerous functions and components. The microcontroller module 34 includes an input/output (not shown) connection internal memory (not shown) or a connection to external memory (not shown), a CPU, a memory/data storage unit (not shown) and so forth. The data storage can be used to store the one or more parameters, the feedback, a status, diagnostic information or a combination thereof. The data storage can be a REID tag, a magnetic strip, a memory or a combination thereof. A power source 36 is contained within the housing 12 to provide an internal source of power to drive the internal components and various modules. The power source 36 may be an internal battery, replaceable battery, rechargeable battery, generator, chemical cell or other source known to the skilled artisan. Alternatively, the power source 36 may be directly connected to an external power source e.g., 12 v source, electrical outlet, USB port, computer battery or other source of electrical power.

A motor module 38 is also contained within the housing 12 and in communication with the various modules. The motor 38 includes an output shaft 40 for transferring the energy to one or more sets of gears (not shown) located in gear box 42. The gear box 42 also includes an output shaft that is ultimately used to drive the rotating shaft 28 and strut fitting 30. A rotational shaft encoder 46 and a strut identifier module 48 may be located between the motor module 38 and the strut fitting 30. The rotational shaft encoder 46 collects data relating to the rotation of the rotating shaft 28 or various output shafts (not shown). In addition, the programmable tool may include an integral torque sensor and limiter which measures the amount of torque and limits the torque that can be transmitted by the motor module 38 to the rotating shaft 28 in known fashion, e.g. by switching off the motor module 38 in the case of an electric motor module 38 or in a similar manner. Alternatively the gear box 42 or the motor module 38 may include a clutch mechanism to limit the torque supplied to the rotating shaft 28.

Figure 3:
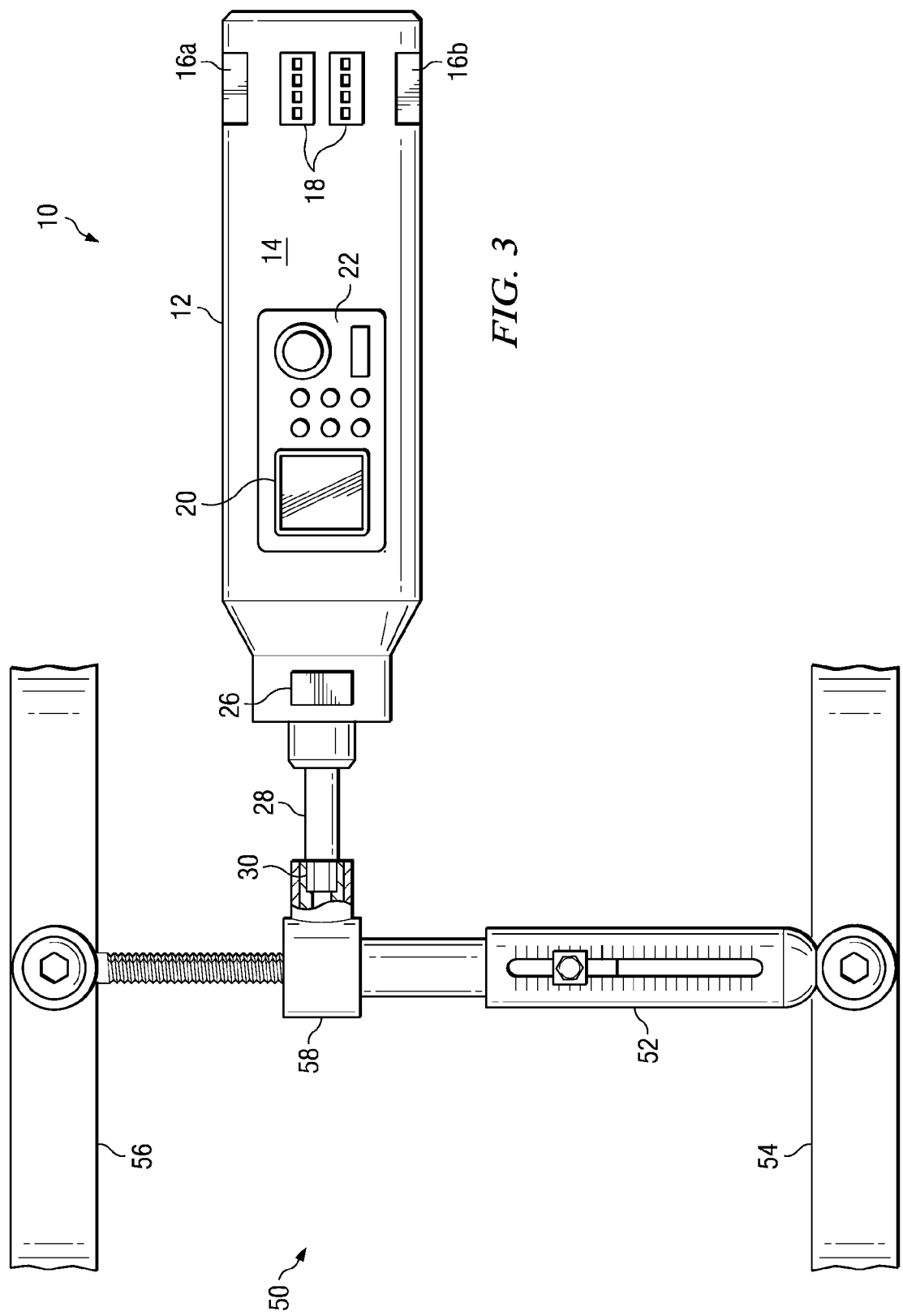
FIG. 3 is a perspective view of one embodiment of a programmable tool for external fixator strut length adjustment.

FIG. 3 is a perspective view of one embodiment of a programmable tool for external fixator strut length adjustment. In operation, the programmable tool 10 is used to adjust an external fixation device 50. The external fixation device 50 includes numerous struts 52 separating a first 54 and a second 56 fixation rings. For simplicity, a portion of the external fixation device 50 including a portion of the first 54 and second 56 fixation rings separated by a single strut 52 is shown. The strut 52 includes a strut adjustment mechanism 58 adapted to fit the strut fitting 30 of the programmable tool 10. The programmable tool 10 includes a housing 12 having a front 14 and a back (not shown). The shape of the housing 12 may be in any shape and size convenient for use. The housing 12 also has one or more data ports 18 that allow communication from the programmable tool 10 and an external source, e.g., computer, etc. The one or more data ports 18 are connected to the internal circuitry (not shown) of the programmable tool 10. For example, in one embodiment the housing 12 has a power connection 16a and 16b to provide a source of external power to recharge the batteries (not shown) used to operate the programmable tool 10. The housing 12 also includes a control board 22 that has various controls to allow the user to operate various functions of the device. For example, the control board 22 may include selectors for the specific struts, buttons to set the time, date, etc. and other selectors that allow programming or operation of various functions in conjunction with the display 20.

In operation, the strut adjustment mechanism 58 of the strut 52 is adapted to fit the strut fitting 30 of the programmable tool 10. The strut sensor 26 identifies each individual specific strut 52 on the external fixation device and the programmable tool 10 then adjusts that strut 52 to the specific length prescribed by the treatment protocol. The procedure is repeated for each strut 52 of the external fixation device 50. In some embodiments, after making the length adjustments, the programmable tool 10 updates the adjustment instructions stored in a memory unit in the microcontroller 34 (shown in FIG. 2) with relevant information, such as the length of the strut after an adjustment, the amount of adjustment, or the number of times adjustments have been made.

Figure 4:
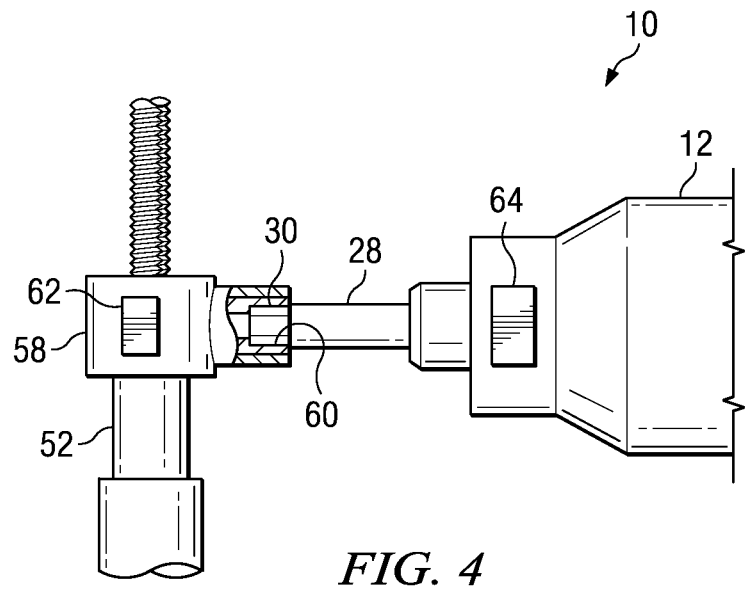
FIG. 4 is a perspective view of one embodiment of a strut number identifier of a programmable tool for external fixator strut length adjustment.

FIG. 4 is a perspective view of one embodiment of a strut number identifier of a programmable tool for external fixator strut length adjustment. In operation, the programmable tool 10 is used to adjust a strut 52 separating a first (not shown) and a second (not shown) fixation rings. The strut 52 includes a strut adjustment mechanism 58 adapted to fit the strut fitting 30 of the programmable tool 10. The programmable tool 10 includes a housing 12 having a front and a back (not shown). The shape of the housing 12 may be in any shape and size convenient for use. The strut adjustment mechanism 58 includes an indention 60 that is adapted to fit the strut fitting 30 to provide secure connection between the strut 52 and the programmable tool 10. Each of the specific strut 52 includes a strut specific RF transmitter 62 that contains the necessary information for the specific strut 52. The programmable tool 10 includes a RF sensor 64 that receives the information from the RF transmitter 62 to identify the specific strut 52. The RF sensor 64 is in communication with the microcontroller module (not shown) and is used to automatically adjust the length of the strut 52.

Figure 5:
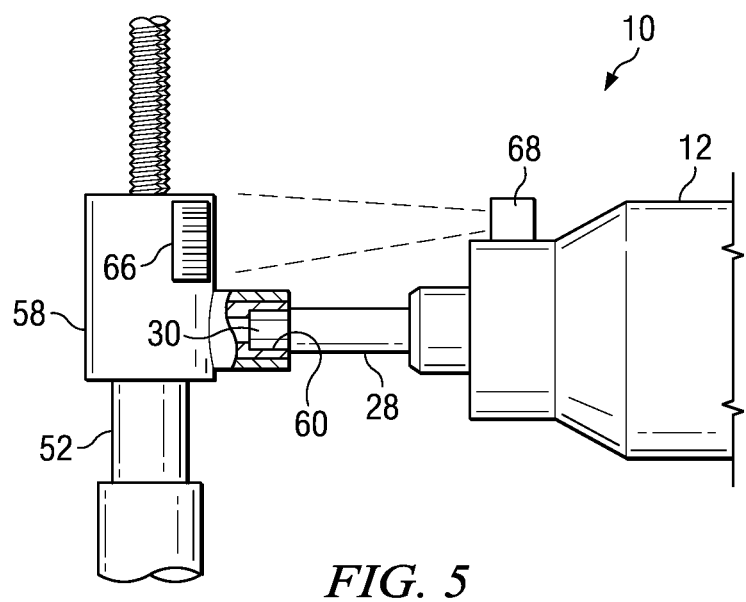
FIG. 5 is a perspective view of one embodiment of a strut number identifier of a programmable tool for external fixator strut length adjustment.

FIG. 5 is a perspective view of another embodiment of a strut number identifier of a programmable tool for external fixator strut length adjustment. In this embodiment, the programmable tool 10 is used to adjust a strut 52 separating a first (not shown) and a second (not shown) fixation rings. The strut 52 includes a strut adjustment mechanism 58 adapted to fit the strut fitting 30 of the programmable tool 10. The strut adjustment mechanism 58 includes an indention 60 that is adapted to fit the strut fitting 30 to provide secure connection between the strut 52 and the programmable tool 10. Each of the specific struts 52 includes a strut specific bar code 66 that contains the identification information for the specific strut 52. The programmable tool 10 includes a housing 12 having a front and a back (not shown). The shape of the housing 12 may be in any shape and size convenient for use. The programmable tool 10 includes a bar code reader 68 that reads the information from the bar code 66 to identify the specific strut 52. The bar code reader 68 is in communication with the microcontroller module (not shown) and is used to automatically adjust the length of the strut 52.

Figure 6:
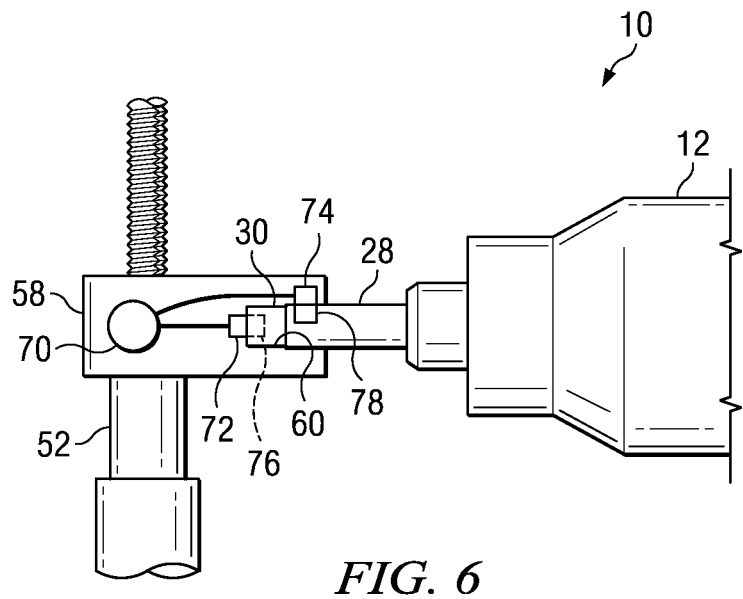
FIG. 6 is a perspective view of one embodiment of a strut number identifier of a programmable tool for external fixator strut length adjustment.

FIG. 6 is a perspective view of another embodiment of a strut number identifier of a programmable tool for external fixator strut length adjustment. In this embodiment, the programmable tool 10 is used to adjust a strut 52 separating a first (not shown) and a second (not shown) fixation rings. The strut 52 includes a strut adjustment mechanism 58 adapted to fit the strut fitting 30 of the programmable tool 10. The strut adjustment mechanism 58 includes an indention 60 that is adapted to fit the strut fitting 30 to provide secure connection between the strut 52 and the programmable tool 10. The strut 52 also includes an strut identification device 70 for storing and providing strut identification information. The indention 60 is adapted to include a first electrical contact 72 and/or a second electrical contact 74 connected to the strut identification device 70. The first and second contacts 72 and 74 engage corresponding electrical contacts 76 and 78 of the programmable tool 10, respectively. The programmable tool 10 includes the first electrical contact 76 and the second contact 78 for receiving/reading a signal from the strut identification device 70 via the first and second contact 72 and 74. The programmable tool 10 is in communication with the microcontroller module (not shown) and is used to automatically adjust the length of the strut 52.

Figure 7:
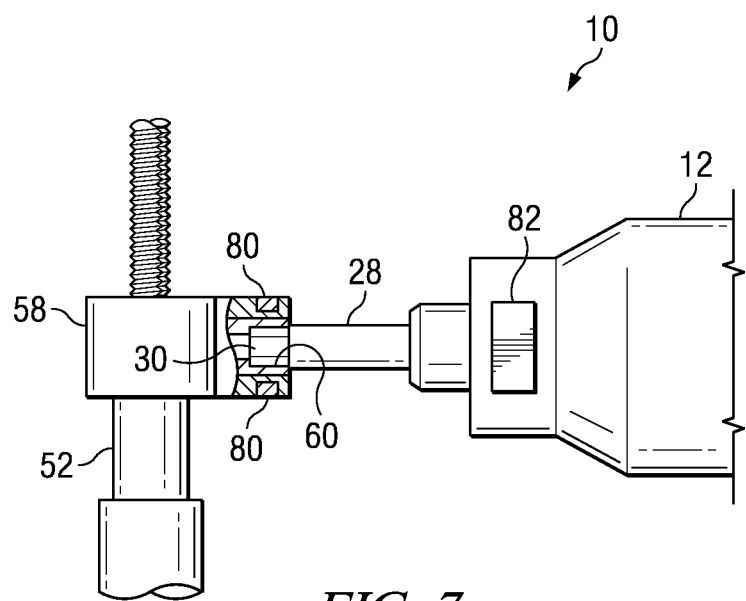
FIG. 7 is a perspective view of one embodiment of a strut rotation encoder of a programmable tool for external fixator strut length adjustment.

FIG. 7 is a perspective view of another embodiment of a strut rotation encoder of a programmable tool for external fixator strut length adjustment. In this embodiment, the programmable tool 10 is used to adjust a strut 52 separating a first (not shown) and a second (not shown) fixation rings. The strut 52 includes a strut adjustment mechanism 58 adapted to fit the strut fitting 30 of the programmable tool 10. The strut adjustment mechanism 58 includes an indention 60 that is adapted to fit the strut fitting 30 to provide secure connection between the strut 52 and the programmable tool 10. The strut adjustment mechanism 58 includes a magnetic ring 80 about the indention 60 and the strut fitting 30 of the programmable tool 10. The programmable tool 10 includes a housing 12 having a front and a back (not shown). The shape of the housing 12 may be in any shape and size convenient for use. The programmable tool 10 includes a magnetic feedback sensor 82, which allows monitoring of the number of turns made by the strut adjustment mechanism 58. Since the number of turns can be correlated to the amount of length adjustment, corresponding change in length of the strut 52 can be determined.

FIG. 8 is a perspective view of one embodiment of a digital ruler (A) of a programmable tool for external fixator strut length adjustment and a method of strut length measurement using a digital ruler (B).

Figure 8B:
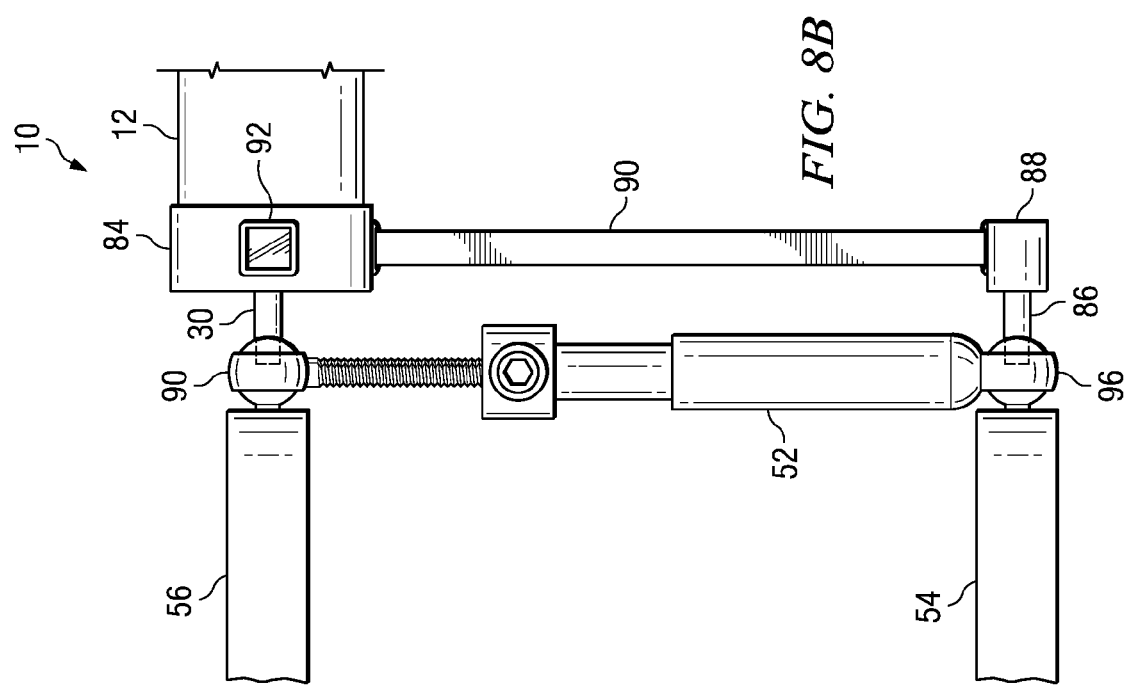
FIG. 8 is a perspective view of one embodiment of a digital ruler (A) of a programmable tool for external fixator strut length adjustment and a method of strut length measurement using a digital ruler (B).
Figure 8A:
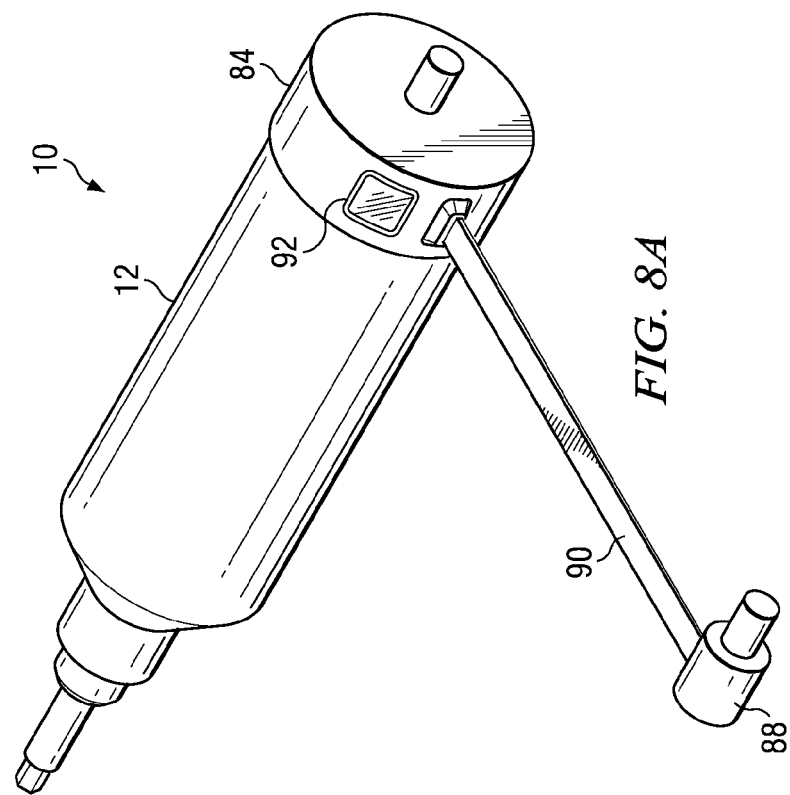

FIG. 8A is an image of another embodiment, the programmable tool 10 used to adjust a strut (not shown) to separate a first (not shown) and a second (not shown) fixation rings. The programmable tool 10 includes a housing 12 having a front and a back (not shown). The housing 12 may have a variety of connections ports, connectors, displays and controls (not shown). The housing 12 also has one or more data ports (not shown) that allow communication between the programmable tool 10 and an external source, e.g., computer, etc (not shown). The housing 12 includes a display (not shown) which may display various types of information. The housing 12 also includes a control board (not shown) that has various controls to allow the user to operate various functions of the programmable tool 10. The control board (not shown) may also include an on/off switch (not shown) that may be used to operate the programmable tool 10. The housing 12 has a rotating shaft (not shown) that extends from the housing 12 and terminates in a strut fitting (not shown) that allows the connection of the programmable tool 10 to an external fixation strut. The rotating shaft (not shown) may be enclosed in a separate covering leaving only the strut fitting (not shown) exposed and accessible, while protecting the actual rotating shaft (not shown). The programmable tool 10 includes a measuring device 84 to measure the distance between the first strut fitting 30 and a second strut fitting 86 attached to a second strut fitting housing 88 that is separated by a measuring segment 90. The programmable tool 10 is calibrated to allow the measuring device 84 to measure the length of the measuring segment 90 and in turn the distance separating the first strut fitting 30 and the second strut fitting 86. The distance may be displayed on a display 92 and/or transmitted to the programmable tool 10 for automatic adjustment of the strut (not shown).

FIG. 8B is an image of a programmable tool 10 in operation. The programmable tool 10 used to adjust a strut 52 to move a first fixation ring 56 relative to a second fixation ring 54. The programmable tool 10 includes a housing 12 having a front and a back (not shown). The housing 12 has a first strut fitting 30 that allows the connection of the programmable tool 10 to a first ball joint 94 of an external fixation strut 52. The programmable tool 10 includes a measuring device 84 to measure the distance between the first strut fitting 30 and a second strut fitting 86 that is separated by a measuring segment 90; the second strut fitting 86 is attached to a second strut fitting housing 88. The second strut fitting 86 fits a second ball joint 96 of an external fixation strut 52. The programmable tool 10 is calibrated to allow the measuring device 84 to measure the length of the measuring segment 90 and in turn the distance separating the first ball joint 94 and the second ball joint 96 and, therefore, the distance separating the first fixation ring 56 and the second fixation ring 54. The distance may be displayed on a display 92 and/or transmitted to the programmable tool 10 for automatic adjustment of the strut (not shown).

To facilitate the understanding of this application, a number of terms are defined below. Terms defined herein have meanings commonly understood by a person of ordinary skill in the areas relevant to the present application. Terms such as "a", "an" and "the" are not intended to refer to only a singular entity, but include the general class of which a specific example may be used for illustration. The terminology herein is used to describe specific embodiments of the disclosure, but their usage does not delimit the disclosure, except as outlined in the claims.

Figure 9:
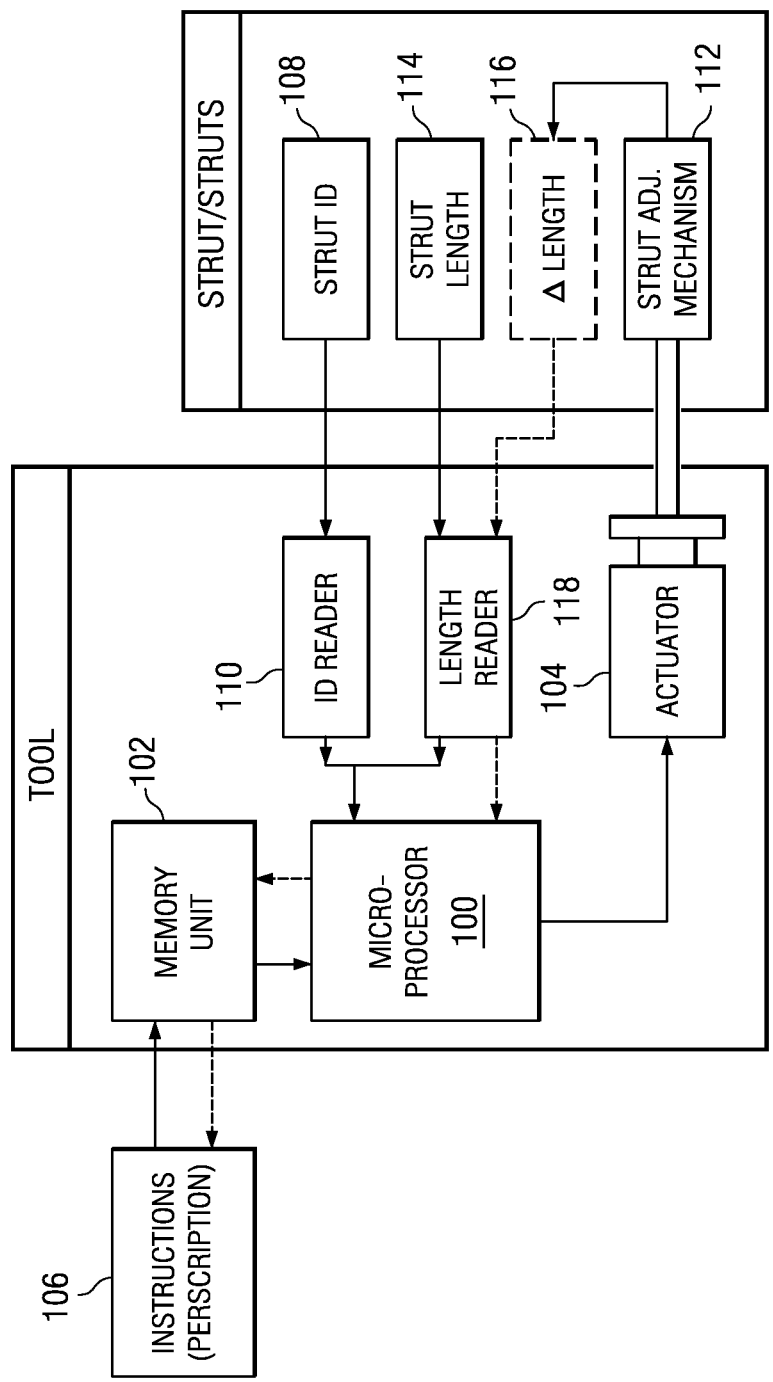
FIG. 9 is a schematic block diagram of one embodiment of a method of adjusting an external fixation strut.

Referring to FIG. 9, the present disclosure includes a method for adjusting the orientation of a first external support member relative to a second external support member, in which a plurality of adjustable struts connect the first and second external support members. The method includes providing a programmable tool, which can be any tool described in the present application. In some embodiments, the programmable tool comprises a controller 100 in electrical communication with a memory unit 102 and an actuator 104. The actuator 104 is operable to engage the plurality of adjustable struts and adjust the length of the plurality of adjustable struts. In some embodiment, the actuator 104 is operable to engage and rotate a rotatable adjustment mechanism 112 of the struts to effect the desired length adjustment. The rotatable adjustment mechanism 112 can include any adjustment mechanism described in or modified in accordance to the present disclosure. The method further includes storing, in the memory unit 102, instructions 106 for adjusting the length of each of the plurality of adjustable struts to a desired length. In some embodiments, the instructions 106 includes a prescription table for bone realignment. The method further includes receiving identification information 108 corresponding to the first adjustable strut. The identification information 108 can include any information that is described in the present disclosure or known in the art for uniquely identifying one strut from the other struts. In some embodiments, the identification information 108 is provided from a signal emitter in the strut to a signal receiver 110 in the programmable tool. The method further includes retrieving, from the memory unit 102, the instructions for adjusting the length of the identified strut based on the identification information 108 and activating the actuator 104 to adjust the length of the identified strut according to the retrieved instructions. As a result the identified strut is adjusted to a desired length.

In some embodiments, the programmable tool further includes a measuring device 118 for measuring the length of the plurality of adjustable struts, and the method further includes determining the length of the first adjustable strut prior to and after adjusting the length of the first adjustable strut and confirming that the first strut has the desired length 114. In some embodiments, information such as the desired strut length 114 or the change in strut length 116 can be fed back to the controller 100 to be stored in the memory unit 102. In yet some other embodiments, the feedback information stored in the memory unit 102 could be used by a doctor or a user as a record to verify that the instructions 106 have been carried out or to update or optimize the instructions 106.

The present application provides a method and a tool for incrementally adjusting the length of an external fixator strut or other connection rod of an external fixation device. The external fixation device may include a first external fixator ring and a second external fixator ring connected by one or more external fixator struts or connecting rods. In some embodiments, there are a plurality of external fixator struts that include a first ball joint having a first ball stud extending from a first ball that is at least partially surrounded by a first ball cage. The first ball stud attaches to an aperture in an outer or inner surface of the external fixator ring or other external support. The external fixation strut includes a strut housing comprising an axial bore extending longitudinally from the ball cage and an adjustment sleeve slidably fitted within the axial bore of the strut housing and a sleeve fastener positioned to secure the adjustment sleeve to the strut housing. The adjustment sleeve adjusts coarse rapid longitudinal movement with respect to the strut housing and an adjustment mechanism positioned at one end of the adjustment sleeve and threadably connected to a threaded elongated member. The adjustment mechanism gradually adjusts longitudinally the threaded elongated member and a second ball joint connected to the threaded elongated member. The second ball joint includes a second ball stud extending from a second ball that is at least partially surrounded by a second ball cage. The second ball stud attaches to an aperture in an outer or inner surface of the external fixator ring or other external support.

The present application includes a tool that can incrementally adjust the overall end-to-end length of the external fixator strut or other connection rod of an external fixation device. The tool is adapted to engage the adjustment mechanism of the external fixator strut and rotate the adjustment mechanism the preprogrammed direction and amount of turns to adjust the position of the threaded elongated member relative to the adjustment mechanism of the external fixator strut and thereby automatically adjust the overall end-to-end length of the external fixator strut the prescribed amount.

The present application also includes a method of incrementally adjusting the overall end-to-end length of the external fixator strut or other connection rod of an external fixation device by programming a programmable tool with the direction and amount of external fixation strut adjustment, engaging a programmable tool to the adjustment mechanism of the strut and allowing the tool to turn the adjustment mechanism of the strut in pre-programmed direction and on the pre-programmed amount of adjustment. The tool is adapted to engage the adjustment mechanism of the external fixator strut and rotate the adjustment mechanism by the pre-programmed amount of turns to adjust the position of the threaded elongated member relative to the adjustment mechanism of the external fixator strut. In some embodiments, the tool includes a recognition mechanism for receiving identification information corresponding to the strut to be adjusted, and automatically identifying the strut based on the identification information. Upon recognizing the strut, the tool is operable to automatically adjust the overall end-to-end length of the external fixator strut the prescribed amount.

In one embodiment, the tool has a housing, a strut number identifier, a microcontroller with an internal memory, a control board, a power source, a motor, a gear box and a rotating shaft that engages an adjustment mechanism of the external fixator strut. In operation, the tool is positioned in or about the adjustment mechanism of a first external fixator strut and activated. The tool uniquely identifies the external fixator strut and retrieves the direction and amount of length adjustment that should be performed for this external fixator strut. In some embodiments, the tool may be configured to identify and control struts from more than one external fixation device. The rotating shaft engages the adjustment mechanism of the external fixator strut and rotates the adjustment mechanism by the desired number of turns. The tool is then repositioned about the adjustment mechanism of a second external fixator strut to repeat the process of strut length adjustment until all external fixator struts are adjusted.

The strut number identifier may include a variety of mechanisms known to the skilled artisan. One common method of identification includes a radiofrequency (RF) sensor that wirelessly communicates with a radio frequency transmitter (RFID) located on the adjustment mechanism of the external fixator strut. Another strut number identifier may include a bar code reader that counts a specific number of grooves on the adjustment mechanism of the external fixator strut or communicates with magnetic strip located on the adjustment mechanism of the external fixator strut. In another embodiment, strut number identifier includes a sensor that receives information from a touch memory button located on the adjustment mechanism of the external fixator strut. Another embodiment of the present disclosure provides that the strut number is determined manually and allow the tool to engage the adjustment mechanism and rotates the adjustment mechanism on the desired number of turns.

The present application also provides a microcontroller for the strut adjustment tool to handle the operations and computations and an internal memory storage unit to store struts adjustment related data and other necessary records. The memory storage unit may be in the form of a non-volatile memory, magnetic memory, read only memory (ROM), electrically erasable and programmable read only memory (EEPROM) or firmware.

The present application also provides a control board with e.g., a display, a speaker and several control buttons to handle the operations and communication with the patient to perform an external fixator strut's adjustment with the programmable adjustment tool. For example, the present disclosure may include a control board with a tool mode control button that allows switching between reading and adjustment modes. In addition, the present disclosure may provide with different visual, audio, vibration and other signals indicating the status of the adjustment tool (e.g., start signal after strut number identification, adjustment end signal after completion of each length adjustment of the strut, battery recharge signal, emergency signal, adjustment time reminder and so forth).

The tool may be internally powered by a rechargeable battery connected to an external power source (AC, DC, Solar and so forth) through power supply connectors located on the housing of the tool.

The tool may include a geared motor as well as other means to incrementally adjust the overall end-to-end length of the external fixator strut or other connection rod of an external fixation device. For example, the tool may provide electromagnetic impulses to push the elongating member of the strut out of the strut housing. The tool may also have a shape-memory alloy string to push the elongating member of the strut out of the strut housing.

The tool may also include a data port (e.g., USB connector) or a wireless communication port (blue tooth, WiFi, IR, RF, and so forth). Using the data port or wireless communication port, the tool may be connected to data storage (e.g., a memory stick) or to a computer to download the information on prescribed direction and amount of length adjustments for each external fixator strut. In addition, this data transfer may be bi-directional to allow the downloading of specific strut length adjustment parameters (e.g., an actual time of strut adjustment, actual amount of strut adjustment, etc.) that were stored on the internal memory of the tool to memory storage or computer.

The present application may include a device and method for indicating the actual number of turns the rotating shaft of the tool performed during each adjustment. For example, the adjustment tool may include a rotational shaft encoder or other feedback sensor that counts the number of turns of the rotating shaft of the tool.

The present application may also include a device and method for indicating the actual number of turns the adjustment mechanism of the external fixator strut performed during each adjustment. For example, the adjustment tool may include a magnetic feedback sensor communicating with magnetic ring transmitter located on the adjustment mechanism of the external fixator strut that counts the number of turns of the adjustment mechanism of the external fixator strut.

In addition, the present application may also include a device and method for indicating the overall length of the external fixator strut. For example, the present disclosure may include a digital ruler or feedback sensor to determine the overall length and/or length adjustment amount of the external fixator strut.

In addition, the present application may also include a device and method for indicating the resistance during the adjustment of the external fixator strut. For example, the present application may include a feedback torque measurement sensor to monitor resistance during the adjustments of the external fixator strut and provide a turning profile.

The programmable adjustment tool may be in the form of a wrench, a clip or similar device that allows the contacting of the tool with the adjustment mechanism of the external fixator strut so that the tool is secured to the external fixator strut by itself.

In addition to or instead of the displays, an electrical sensor may be provided which generates a signal when the specified target adjustment is obtained. The present application includes conventional displays and alarms in combination to be activated upon attaining a specified target adjustment. The use and arrangement of these displays and alarms in handheld tools are conventionally known to be simple, functionally reliable, and inexpensive. For example, a display can be mechanically activated in a conventional manner, e.g., by an axially movable pin, a pivotably movably mounted bar, etc. Additionally or alternatively, an electrical sensor can be used in a conventional manner to generate a signal when the specified target adjustment is obtained. Signals from the electronic sensor are evaluated in a known manner by an electronic circuit in order to trigger conventional acoustic or optical devices when the target torque is obtained.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

All publications and patent applications mentioned in the specification are indicative of the level of skill of those skilled in the art to which this disclosure pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A programmable tool operable to adjust an external fixation strut having a rotatable adjustment mechanism for length adjustments and a strut identifier operable to provide a signal that identifies the external fixation strut, the programmable tool comprising:
   a housing;
   a power supply disposed in the housing;
   a data port disposed at least partially within the housing, the data port operable to receive instructions for adjusting the external fixation strut;
   a signal-sensor disposed at least partially within the housing, the signal-sensor operable to receive the signal from the strut identifier;
   a motor disposed within the housing, comprising a first output shaft;
   a gear box comprising one or more sets of gears driven by the first output shaft,
   wherein the one or more sets of gears drive a second output shaft;
   a rotational shaft coupled to the second output shaft, the rotational shaft comprising a strut fitting adapted to engage and rotate the rotatable adjustment mechanism of the external fixation strut;
   a controller in electrical communication with the data port, the signal-sensor, the power supply, and the motor;
   a memory unit in electrical communication with the controller, the memory unit operable to store data; and
   wherein the controller is configured to retrieve, from the memory unit, instructions for adjusting a length of the external fixation strut based on the signal received from the strut identifier by the signal-sensor, and
   activate the motor to adjust the length of the external fixation strut according to the retrieved instructions.

2. The tool of claim 1, further comprising a display in electrical communication with the controller, wherein the display comprises a LCD display, a LED display, an array of LEDs, a speaker, a multi-tone generator, a communication interface or a combination thereof.

3. The tool of claim 1, wherein the data port comprises a USB port, an RS232 port, a 25 modem port, cellular modem, a Wi-Fi module, a Bluetooth module, an IR module, an RF module, an RFID module or combination thereof.

4. The tool of claim 1, wherein the signal-sensor comprises a barcode reader, a Bluetooth receiver, an IR receiver, an RF receiver, an RFID receiver, magnetic decoder or combination thereof.

5. The tool of claim 1, wherein the power supply comprises a battery, a DC source, a AC source or a combination thereof.

6. The tool of claim 1, wherein the power supply comprises a rechargeable battery and a connection port for connection to a DC source, a AC source or a combination thereof.

7. The tool of claim 1 wherein the controller comprises a microcontroller, a microcomputer, a programmable logic array, or an application specific integrated circuit under the control of a software program.

8. The tool of claim 1, further comprising a control panel in electrical communication with the controller, the control panel operable to input control signals for one or more operations of the programmable tool.

9. The tool of claim 1, wherein the memory unit is configured to store instructions for adjusting the length of each of a plurality of external fixation struts.

10. A programmable tool operable to adjust an external fixation strut having a rotatable adjustment mechanism for length adjustments and a strut identifier operable to provide a signal that identifies the external fixation strut, the programmable tool comprising:
- a housing;
- a power supply disposed in the housing;
- a data port disposed at least partially within the housing, the data port operable to receive instructions for adjusting the external fixation strut;
- a signal-sensor disposed at least partially within the housing, the signal-sensor operable to receive the signal from the strut identifier;
- a motor disposed within the housing;
- an output shaft driven by the motor, the output shaft comprising a strut fitting adapted to engage and rotate the rotatable adjustment mechanism of the external fixation strut;
- a controller in electrical communication with the data port, the signal-sensor, the power supply and the motor; and
- wherein the controller is configured to retrieve, from a memory unit, instructions for adjusting a length of the external fixation strut based on the signal received from the strut identifier by the signal-sensor, and
- activate the motor to adjust the length of the external fixation strut according to the retrieved instructions.

11. The tool of claim 10, further comprising a display comprises a LCD display, a LED display, an array of LEDs, a speaker, a multi-tone generator, a communications interface or a combination thereof.

12. The tool of claim 10, wherein the data port comprises a modem, cellular modem, a Wi-Fi module, a Bluetooth module, an IR module, an RF module, an RFID module or combination thereof.

13. The tool of claim 10, wherein the signal-sensor comprises a barcode reader, a Bluetooth receiver, an IR receiver, an RF receiver, an RFID receiver, magnetic decoder or combination thereof.

14. The tool of claim 10, wherein the power supply comprises a battery, a DC source, a AC source or a combination thereof.

15. The tool of claim 10, further comprising a gear box, a clutch or both coupling the output shaft and the motor.

16. The tool of claim 10 further comprising a memory unit in electrical communication with the controller to store one or more parameters.

17. The tool of claim 10, further comprising a display in electrical communication with the controller.

18. The tool of claim 10, further comprising a control board in electrical communication with the controller to control one or more operations of the programmable tool.

19. The tool of claim 10, wherein the controller comprises a digital logic circuit selected from a microcontroller, microcomputer, a programmable logic array, an application specific integrated circuit under the control of a software program.

* * * * *